(12) United States Patent
Yang (10) Patent No.: US 9,861,814 B2
(45) Date of Patent: Jan. 9, 2018

(54) MEDICAL ELECTRICAL LEAD HAVING BIOLOGICAL SURFACE AND METHODS OF MAKING AND USING SAME

(75) Inventor: Zhongping C. Yang, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 1648 days.

(21) Appl. No.: 12/977,655

(22) Filed: Dec. 23, 2010

(65) Prior Publication Data

US 2012/0165913 A1 Jun. 28, 2012

(51) Int. Cl.
*A61F 2/06* (2013.01)
*A61N 1/05* (2006.01)

(52) U.S. Cl.
CPC .................................. *A61N 1/056* (2013.01)

(58) Field of Classification Search
CPC .................................. A61L 27/34; A61L 31/10
USPC .......................................... 607/115, 116, 130
See application file for complete search history.

(56) References Cited

U.S. PATENT DOCUMENTS

| | | |
|---|---|---|
| 4,521,564 A | 6/1985 | Solomon et al. |
| 4,979,959 A | 12/1990 | Guire |
| 5,308,641 A | 5/1994 | Cahalan et al. |
| 5,811,151 A | 9/1998 | Hendriks et al. |
| 5,866,113 A | 2/1999 | Hendricks et al. |
| 5,925,552 A | 7/1999 | Keogh et al. |
| 6,033,719 A | 3/2000 | Keogh |
| 6,096,070 A | 8/2000 | Ragheb et al. |
| 6,159,531 A | 12/2000 | Dang et al. |
| 6,444,254 B1 | 9/2002 | Chilkoti et al. |
| 6,961,610 B2 | 11/2005 | Yang et al. |
| 7,037,332 B2 * | 5/2006 | Kutryk et al. ............... 623/1.48 |
| 7,163,712 B2 | 1/2007 | Chilkoti et al. |
| 7,309,593 B2 | 12/2007 | Ofstead et al. |
| 7,353,067 B1 * | 4/2008 | Helland et al. ............... 607/130 |
| 7,519,409 B2 | 4/2009 | Yang et al. |
| 7,547,445 B2 | 6/2009 | Chudzik et al. |
| 7,550,443 B2 | 6/2009 | Stucke et al. |
| 7,550,444 B2 | 6/2009 | Stucke et al. |
| 7,632,234 B2 | 12/2009 | Manda et al. |
| 7,769,451 B2 | 8/2010 | Yang et al. |
| 7,801,623 B2 | 9/2010 | McVenes et al. |
| 2003/0059537 A1 | 3/2003 | Chilkoti et al. |
| 2003/0204230 A1 | 10/2003 | Yang et al. |

(Continued)

FOREIGN PATENT DOCUMENTS

| | | |
|---|---|---|
| WO | WO 2006/063181 | 6/2006 |
| WO | WO 2006/091675 | 8/2006 |
| WO | WO 2008/008253 | 1/2008 |

OTHER PUBLICATIONS

Rossi et al., "Reply to the article by Wendel HP et al.: Endothelial progenitor cell capture stents—hype or hope?" International Journal of Cardiology, Nov. 5, 2010; 145(1):117-118.

(Continued)

*Primary Examiner* — Michael D Abreu (57) ABSTRACT

An implantable electrical lead suitable for left sided cardiac placement, the implantable medical electrical lead having an external blood contacting surface having an external coating including a monolayer of at least one biological agent that promotes endothelialization covalently attached to a polymeric lead surface.

20 Claims, 5 Drawing Sheets

(56) References Cited

U.S. PATENT DOCUMENTS

| | | | |
|---|---|---|---|
| 2004/0161853 | A1 | 8/2004 | Yang et al. |
| 2005/0027175 | A1 | 2/2005 | Yang |
| 2005/0049472 | A1 | 3/2005 | Manda et al. |
| 2005/0137669 | A1 | 6/2005 | Krishnan et al. |
| 2005/0244453 | A1 | 11/2005 | Stucke et al. |
| 2006/0240072 | A1 | 10/2006 | Chudzik et al. |
| 2006/0247692 | A1 | 11/2006 | Yang et al. |
| 2007/0087114 | A1 | 4/2007 | Chilkoti et al. |
| 2007/0154519 | A1 | 7/2007 | Yang |
| 2007/0154893 | A1 | 7/2007 | Yang et al. |
| 2007/0233217 | A1 | 10/2007 | Yang et al. |
| 2007/0299490 | A1 | 12/2007 | Yang et al. |
| 2008/0004670 | A1 | 1/2008 | McVenes et al. |
| 2008/0063627 | A1 | 3/2008 | Stucke et al. |
| 2009/0047413 | A1 | 2/2009 | Yang et al. |
| 2009/0270962 | A1 | 10/2009 | Yang et al. |
| 2010/0042110 | A1 | 2/2010 | Kelley et al. |
| 2010/0056885 | A1 | 3/2010 | Manda et al. |
| 2010/0174351 | A1* | 7/2010 | Ng et al. .................... 623/1.1 |
| 2010/0203100 | A1 | 8/2010 | Cobian et al. |
| 2010/0285084 | A1 | 11/2010 | Yang et al. |
| 2010/0310756 | A1 | 12/2010 | McVenes et al. |
| 2010/0317629 | A1 | 12/2010 | Gallagher et al. |

OTHER PUBLICATIONS

Aoki et al., "Endothelial progenitor cell capture by stents coated with antibody against CD34: The HEALING-FIM (Healthy Endothelial Accelerated Lining Inhibits Neointimal Growth-First in Man) Registry," *Journal of the American College of Cardiology*, 2005; 45(10):1574-1579.

Avci-Adali et al., "New strategies for in vivo tissue engineering by mimicry of homing factors for self-endothelialisation of blood contacting materials," *Biomaterials*, 2008; 29:3936-3945.

Barbato et al., "Autologous cell therapy for enhanced endovascular repair after coronary stent implantation," *EuroIntervention*, 2011; 6:794-795, 797. Available only on the Internet <URL: http://www.pcronline.com/eurointervention/33rd_issue/136/index.php?ind=2>.

Beijk et al., "Genous™ endothelial progenitor cell capturing stent vs. the Taxus Liberté stent in patients with de novo coronary lesions with a high-risk of coronary restenosis: a randomized, single-centre, pilot study," *European Heart Journal*, 2010; 31:1055-1064.

"CD34 (BI-3C5): sc-19621" datasheet [online]. Santa Cruz Biotechnology, Inc., Santa Cruz, CA [retrieved on Dec. 10, 2010]. Retrieved from the Internet: <URL: http://datasheets.scbt.com/SC-19621.pdf>; 1 pg.

Chinn et al., "Extracellular matrix protein coatings promote rapid stent endothelialization," SurModics, Inc., Eden Prairie, MN, [retrieved on Oct. 8, 2010]. Retrieved from the Internet: <URL: www.surmodics.com/pdf/tctpresentation.pdf>; 19 pgs. Presented at Transcatheter Cardiovascular Therapeutics Conference (TCT 2006), Washington, DC, Oct. 22-27, 2006.

Chong et al., "Beyond cell capture: antibody conjugation improves hemocompatibility for vascular tissue engineering applications," *Tissue Engineering: Part A*, 2010; 16(8):2485-2495.

"Diagnosing hemo(in)compatibility: from clinical and device considerations to bench assessment," Surmodics, Inc., Eden Prairie, MN, 2004. Retrieved from the Internet: <URL: http://www.surmodics.com/pdf/HemoCompWP.pdf>; 4 pgs.

"Endothelial progenitor cell (EPC) capture technology for the prevention of in-stent thrombosis and restenosis" datasheet. Orbus Medical Technologies, Ft. Lauderdale, Florida, May 18, 2004; 9 pgs.

Ibrahim, "Hyaluronic acid cues for functional endothelialization of vascular constructs," *J. Tissue Eng. Regen. Med.*, Jan. 2008; 2(1):22-32.

Jun et al., "Development of a YIGSR-peptide-modified polyurethaneurea to enhance endothelialization," *J. Biomater. Sci. Polymer Edn.*, 2004; 15(1):73-94.

Li et al., "Oriented immobilization of anti-CD34 antibody on titanium surface for self-endothelialization induction," *J. Biomed. Mater. Res. A*, Sep. 15, 2010; 94A(4):1283-1293. Published online May 10, 2010.

Lin et al., "In situ endothelialization of intravascular stents coated with an anti-CD34 antibody functionalized heparin-collagen multilayer," *Biomaterials*, 2010; 31:4017-4025.

Meyhoefer et al., "Closure of the subclavian artery puncture site with a percutaneous suture device after removal of an arterial pacemaker lead," *Europace*, 2006; 8:1070-1072.

"Pacific Blue™ anti-human CD34 Antibody" datasheet [online]. BioLegend, Inc., San Diego, CA, 2010 [retrieved on Sep. 14, 2010]. Retrieved from the Internet: <URL: http://www.biolegend.com/pacific-blue-anti-human-cd34-antibody-6143.html>; 2 pgs.

"PhotoLink® Technology" datasheet [online]. SurModics, Inc., Eden Prairie, MN, [retrieved on Oct. 8, 2010]. Retrieved from the Internet: <URL: www.surmodics.com/technologies-surface-hydrophilic-photolink.html>; 2 pgs.

Rotmans et al., "In vivo cell seeding with anti-CD34 antibodies successfully accelerates endothelialization but stimulates intimal hyperplasia in porcine arteriovenous expanded polytetrafluoroethylene grafts," *Circulation*, 2005; 112:12-18; originally published online Jun. 27, 2005.

Serruys, "Endothelial progenitor cell capture technology for the prevention of in-stent thrombosis and restenosis," *The Thoraxcentre Journal*, 2003; 15(3):78-79.

Stokes et al., "The encapsulation of polyurethane-insulated transvenous cardiac pacemaker leads," *Cardiovascular Pathology*, Jul.-Sep. 1995; 4(3):163-171.

Szmitko et al., "Endothelial progenitor cells: new hope for a broken heart," *Circulation*, 2003; 107:3093-3100.

Szmitko et al., "Endothelial progenitor cell-coated stents under scrutiny," *Can. J. Cardiol.*, Nov. 2006; 22(13):1117-1119.

Wendel et al., "Endothelial progenitor cell capture stents—hype or hope?" *Int. J. Cardiol.*, Nov. 5, 2010; 145(1):115-117; Epub Jul. 3, 2009.

(PCT/US2011/066037) PCT Notification of Transmittal of the International Search Report and the Written Opinion of the International Searching Authority.

* cited by examiner

— Covalent bonded biological monolayer
— Conductor
— Inner insulation
— Outer insulation

MEDICAL ELECTRICAL LEAD HAVING BIOLOGICAL SURFACE AND METHODS OF MAKING AND USING SAME

BACKGROUND

Medical electrodes have wide clinical application in conjunction with a variety of electronic implantable medical devices such as pacemakers, cardiovertor defibrillators, neurostimulators, and ECG monitors. Medical leads may carry one or more electrodes used for sensing electrical signals in the body, such as intracardiac electrogram (EGM) signals, electrocardiogram (ECG) signals, and electromyogram (EGM) signals. Electrodes are also used for delivering therapeutic electrical stimulation pulses or for delivering electrical pulses used in electrophysiological mapping or for other diagnostic purposes.

The typical materials used in the manufacture of medical leads, such as, for example, metals such as platinum, titanium, tantalum, stainless steel, iridium, and alloys thereof, are not inherently biocompatible. The response of the body to such a foreign material can be aggressive, resulting in surface-induced thrombus formation. Thrombus formation on the lead can occur within days. Such thrombi can threaten patient health, particularly when they dislodge and travel via the circulatory system.

The left side of the heart pumps blood rich in oxygen to supply all parts of the body, while the right side of the heart pumps blood back to the lungs to pick up more oxygen. Clot formation on a lead placed in the systemic circulation of the left side of the heart can be clinically catastrophic, serving as a source of stroke in patients. While there are clinical applications in which lead placement in the systemic circulation would be advantageous, such left side placement is currently avoided, because of the substantial and potentially devastating risk presented by surface-induced thrombus formation. Thus, there is a clinical need for improved medical leads that are not prone to surface-induced thrombus formation and are suitable for left side placement.

SUMMARY OF THE INVENTION

The present invention includes an implantable electrical lead having an external blood contacting surface having an external coating having a monolayer of at least one biological agent that promotes endothelialization covalently attached to a polymeric lead surface.

The present invention includes an implantable medical electrode having an external blood contacting surface having an external coating having a monolayer of at least one biological agent that promotes endothelialization covalently attached to a polymeric lead surface.

The present invention includes a medical electrical lead having an external blood contacting surface having an external coating having a monolayer of at least one biological agent that promotes endothelialization covalently attached to a polymeric lead surface.

The present invention includes a left side pacing lead having an external blood contacting surface having an external coating having a monolayer of at least one biological agent that promotes endothelialization covalently attached to a polymeric lead surface.

The present invention includes a left side sensing lead having an external blood contacting surface having an external coating having a monolayer of at least one biological agent that promotes endothelialization covalently attached to a polymeric lead surface.

The present invention includes a medical electrical lead suitable for left ventricular placement having an external coating having a monolayer of at least one biological agent that promotes endothelialization covalently attached to a polymeric lead surface.

The present invention includes an endocardial left ventricle lead having an external coating having a monolayer of at least one biological agent that promotes endothelialization covalently attached to a polymeric lead surface.

The present invention also includes implantable medical devices including at least one implantable electrical lead having an external coating having a monolayer of at least one biological agent that promotes endothelialization covalently attached to a polymeric lead surface.

The present invention includes a system suitable for left ventricular placement, the system including at least one implantable electrical lead having an external coating having a monolayer of at least one biological agent that promotes endothelialization covalently attached to a polymeric lead surface.

The present invention includes a method for manufacturing a medical electrical lead suitable for placement in the left ventricle of the heart, the method including covalently attaching a monolayer coating having at least one biological agent that promotes endothelialization to an external blood contacting polymeric surface of the lead.

The present invention includes a method for implanting leads in a left chamber of the heart, the implantable electrical lead having an external blood contacting surface having an external coating having a monolayer of at least one biological agent that promotes endothelialization covalently attached to a polymeric lead surface. In some aspects, the method further includes delivering an electrical stimulus to the heart through the lead. In some aspects, the method further includes sensing an electrical signal through the lead.

The present invention includes a method for left lead placement, the method including placing a lead having an external blood contacting surface having an external coating having a monolayer of at least one biological agent that promotes endothelialization covalently attached to a polymeric lead surface in the left ventricle of the heart. In some aspects, the method further includes delivering an electrical stimulus to the heart through the lead. In some aspects, the method further includes sensing an electrical signal through the lead.

The present invention includes a method for endothelializing an electrical lead placed in the left ventricle of the heart, the method including placing a lead having an external blood contacting surface having an external coating having a monolayer of at least one biological agent that promotes endothelialization covalently attached to a polymeric lead surface in the left ventricle of the heart. In some aspects, the method further includes delivering an electrical stimulus to the heart through the lead. In some aspects, the method further includes sensing an electrical signal through the lead.

The present invention includes a method for promoting the endothelialization of an electrical lead placed in the left ventricle of the heart, the method including placing a lead having an external blood contacting surface having an external coating having a monolayer of at least one biological agent that promotes endothelialization covalently attached to a polymeric lead surface in the left ventricle of the heart. In some aspects, the method further includes delivering an electrical stimulus to the heart through the lead. In some aspects, the method further includes sensing an electrical signal through the lead.

In some aspects of the leads, devices, systems, and methods of the present invention, an implantable electrical lead includes a stimulation lead. In some aspects, an implantable electrical lead includes a sensing lead. In some aspects, an implantable electrical lead is suitable for placement in the left ventricle of the heart.

In some aspects of the leads, devices, systems, and methods of the present invention, the biological agent includes a growth factor. In some aspects, the biological agent includes a polypeptide. In some aspects, the polypeptide includes collagen.

In some aspects of the leads, devices, systems, and methods of the present invention, the biological agent includes a peptide. In some aspects, the biological agent includes a polysaccharide.

In some aspects of the leads, devices, systems, and methods of the present invention, the biological agent includes an antibody. In some aspects, the antibody includes an antibody to an endothelial cell surface marker. In some aspects, the antibody includes an anti-CD34 antibody. In some aspects, the antibody includes an anti-human CD34 antibody.

In some aspects of the leads, devices, systems, and methods of the present invention, a biological agent covalently is attached to the polymeric lead surface by activation by N-hydroxysuccinimide (NHS) and N-ethyl-N'-dimethyl-aminopropyl-carbodiimide hydrochloride (EDC).

In some aspects of the leads, devices, systems, and methods of the present invention, a biological agent is covalently attached to the polymeric lead surface by a dextran linker.

In some aspects of the leads, devices, systems, and methods of the present invention, a biological agent is covalently attached to the polymeric lead surface by sodium periodate chemistry.

In some aspects of the leads, devices, systems, and methods of the present invention, a biological agent is covalently attached to the polymeric lead surface by a UV photo linker.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list. For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

BRIEF DESCRIPTION OF THE FIGURES

FIG. 2 presents an overview of covalently bonded biological lead outer surface.

DETAILED DESCRIPTION OF ILLUSTRATIVE EMBODIMENTS OF THE PRESENT INVENTION

The present invention provides implantable medical electrical leads that are suitable for left sided cardiac placement in oxygenated, arterial blood. The medical electrical leads described herein have an external blood contacting surface that includes an external monolayer coating of at least one biological agent that promotes endothelialization covalently attached to a polymeric lead surface. This external blood contacting surface promotes the endothelialization of the lead. That is, such leads, when placed in contact with the circulatory system, bind, recruit and/or retain circulating endothelial cells (ECs) and/or endothelial progenitors cells (EPCs). Vascular endothelial cells are thin, flattened epithelial cells that form a thin layer on the interior surfaces of all blood vessels and lymphatics (lymph vessels) throughout the entire circulatory system. The thin cell layer formed by endothelial cells is called the endothelium. Both blood and lymphatic capillaries have of a single layer of endothelial cells on the vessel walls that are in contact with circulating blood or lymph. Endothelial cells possess intrinsic characteristics that prevent the formation of blood clots on endothelial surfaces. Thus the endothelium provides an anticoagulant barrier between the vessel wall and blood and plays a major role in inhibiting thrombosis.

The coated medical electrical leads described herein, when placed in contact with the circulatory system, become endothelialized, that is, become covered, in whole or in part, with a layer of viable endothelial cells endothelial cells. This endothelial cell layer serves as an anti-thrombogenic barrier on the surface of the medical electrical lead. The overgrowth and coverage of the lead surface with endothelial cells significantly reduces the thrombogenic potential of the leads. Such endothelialization of the leads results in the reduced adherance of blood components to the lead surface, inhibiting of the formation of blot clots on the lead surface and making such medical electrical leads suitable for left sided cardiac placement in oxygenated, arterial blood. As used herein, the term "endothelial cells" includes endothelial cells at any developmental stage, from endothelial cell progenitors to fully differentiated, mature endothelial cells.

There is currently great concern and clinical avoidance of placing medical electrical leads in the left atrium or left ventricle of the heart. The concern with such left sided placement of a lead is the potential for formation of thromboemboli. Since the left side of the heart pumps the oxygenated blood to all parts of the body, even a small thromboembolus in the systemic circulation can be clinically catastrophic. Possible thromboembolic complications include both thromboembolic cerebral vascular accident (CVA; also referred to as a "stroke") and non-cerebral thromboembolic complications, such as, ischemic lung, splenic infarct, renal infact, and ischemic bowel. The medical electrical leads described herein present a reduced risk of such thromboembolic complications.

Figure 1:
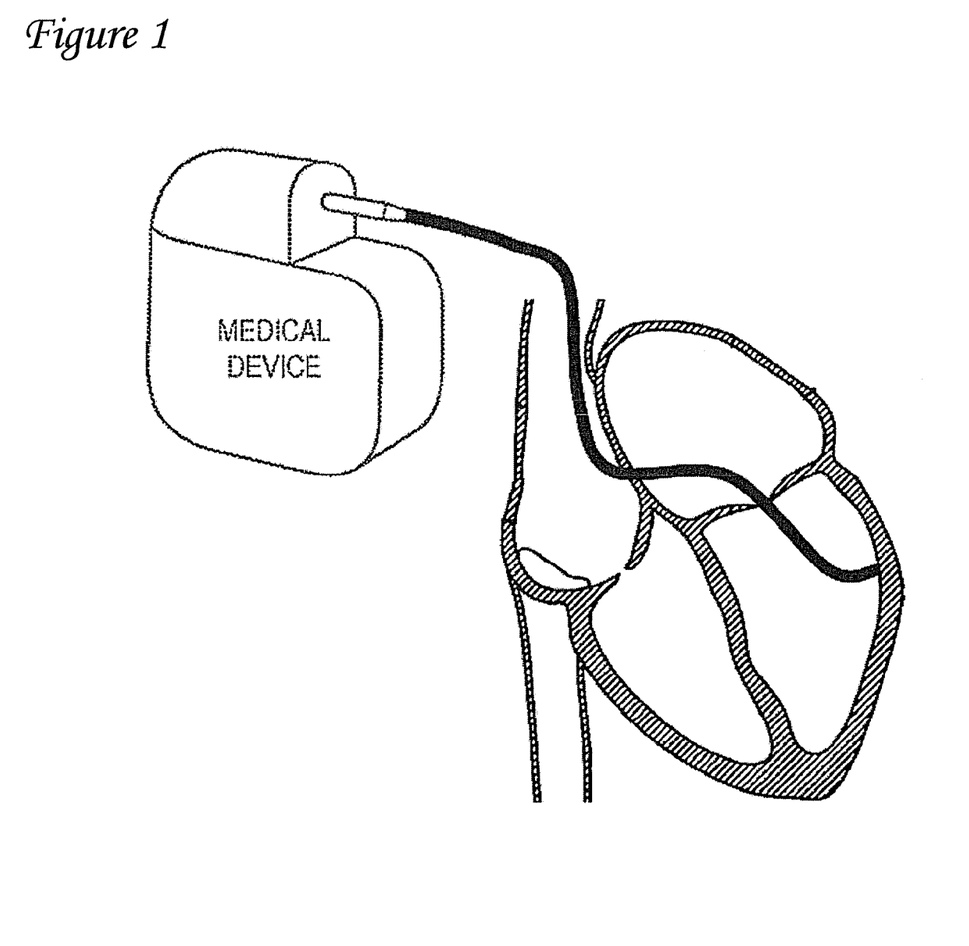
FIG. 1 is a schematic diagram of endocardial left ventricular lead placement in relation to a patient's heart.

The heart is a muscle and functions primarily as a double-sided pump. The left side of the heart pumps blood rich in oxygen to supply all parts of the body, while the right side of the heart pumps blood back to the lungs to pick up more oxygen. There are four chambers, two upper chambers called the left and the right atria and two lower chambers known as the right and left ventricles. Separating these upper and lower chambers there are valves that passively open and close to direct the flow of blood. The left atrium is the left upper chamber of the heart that receives oxygenated blood from the lungs via the pulmonary veins. The left ventricle is the left lower chamber of the heart, which receives oxygenated blood from the left atrium and pumps it through the aorta to the body. The right atrium is the right upper chamber of the heart, which receives deoxygenated blood from the systemic venous system. The right ventricle is the right lower chamber of the heart, which receives deoxygenated blood from the right atrium and pumps it to the lungs via the pulmonary artery. The left ventricle performs the most work and is the strongest of the chambers because it ejects blood into the aorta, the main pipeline that supplies oxygenated blood to the entire body. Coated medical electrical leads as described herein, are suitable for placement in the left ventricle and/or the left atrium (see FIG. 1), also referred to herein as the "left side." Coated medical electrical leads as described herein are also suitable for placement in other locations circulating oxygenated arterial blood, such as for example, coronary arteries, aortic arch vasculature, or peripheral arteries. Coated medical electrical leads as described herein are also suitable for placement in other locations, such as for example, right atrium, coronary sinus, or epidural space of the spinal cord.

As used herein, a thrombus (also referred to herein as "thrombi" or "blood clot") is an aggregate of a network of fibrin, platelets, and other blood components. "Thrombosis" is the formation of such a blood clot. When a thrombus becomes dislodged from the surface on which it formed and circulates in the bloodstream it is called a thromboemboli. As used herein, a thromboembolism is a blood clot which circulates in the bloodstream and blocks a vessel. As used herein, "thrombogenic" is causing, or having the potential to cause, the formation of a thrombus. The endothelialized blood contacting surface of the medical electrical leads described herein prevent the formation of blood clots on lead surfaces and the leads demonstrate a decreased potential for the formation of harmful blood clots.

Figure 2A:
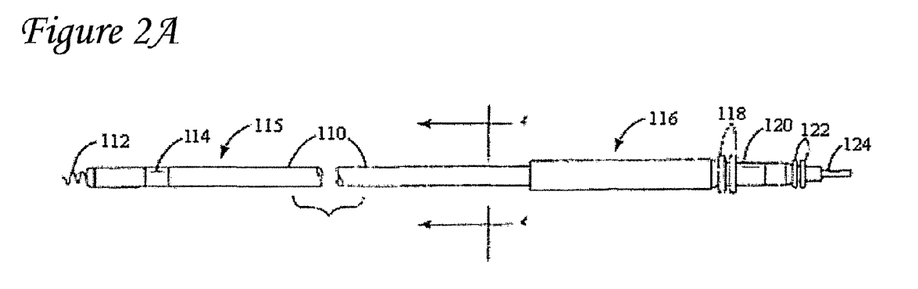
FIG. 2A is a plan view of one embodiment of a medical electrical lead.

An implantable medical electrical lead generally includes an elongated, flexible insulating lead body extending from a proximal end to a distal end, with one or more inner conductors extending through lumens formed in the body and one or more exposed electrodes connected to the distal ends of the conductors. The proximal end is configured to be operatively connected to a pulse generator via a connector. While the electrodes can have any electrode configuration as is known in the art, FIG. 2A is a plan view of one embodiment of a medical electrical lead. Lead 4 includes an elongated lead body 110 extending between a distal end 115 and a proximal end 116. A tip electrode 112 is provided at distal lead end. A ring electrode 114 is spaced proximally from tip electrode 112. Each electrode 112 and 114 is individually coupled to an insulated conductor extending through lead body 115 to a connector 118, 122 or 124 included in proximal connector assembly 120. Proximal connector assembly 120 is adapted to be inserted in a connector bore provided in an implantable medical device for electrically connecting electrodes 112 and 114 to electronics included in, for example, and IMD.

Implantable medical leads have many uses. For example, an implantable electrical medical leads as disclosed herein may be a sensing lead or a stimulation lead. As used herein, a sensing lead carries one or more electrodes used for sensing physiological signals in the body. As used herein, a stimulation lead delivers a therapeutic electrical stimulation pulse, for example, in pacing therapy to the heart, and/or delivers electrical pulses used in electrophysiological mapping or for other diagnostic purposes. A medical electrical lead may be unipolar, bipolar, or multi-polar depending upon the type of therapy to be delivered.

Figure 2B:
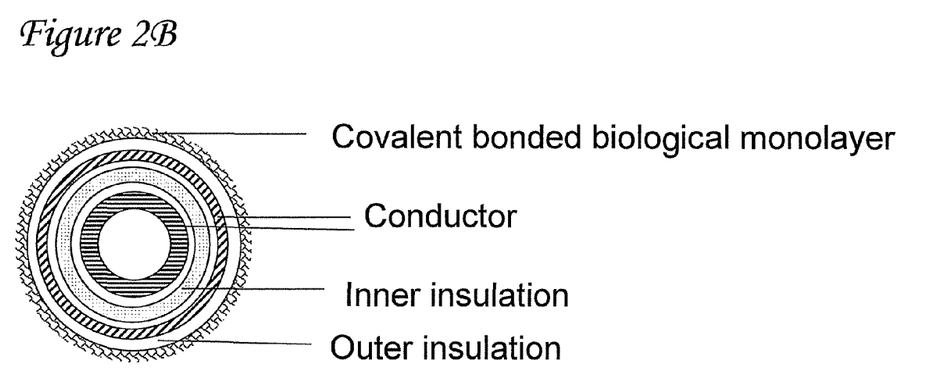
FIG. 2B is a sectional view of an electrical lead provided with a covalently bonded biological lead outer insulation surface.

A medical electrical lead as disclosed herein may have an insulative outer sheath (also referred to herein as an outer insulation). Such an outer sheath may be a polymeric material such as silicone, polyurethane (including, but not limited to the polyether urethanes Pellethane 80A and Pellethane 55D, manufactured by Dow Chemical Company), polytetrafluoroethylene (PTFE), expanded polytetrafluoroethylene (ePTFE), ETFE, polyethylene, polypropylene and other polymer coatings. Such polymeric insulative outer sheaths may be applied by conventional means. With the present invention, the outer insulative sheath of a medical electrical lead is coated with at least one biological agent that promotes endothelialization of the surface of the medical electrical lead. FIG. 2B is a partial cross-sectional view of a coated medical electrical lead, according to an embodiment of the present invention. The one or more biological agents that promote endothelialization may be covalently attached to the insulative outer sheath of the lead body as a monolayer.

In preferred embodiments, the one or more biological agent that promotes endothelialization may be covalently coupled to the polymeric material of the insulative outer sheath of the lead body. Any suitable process may be employed to covalently bond a biological agent to the insulative outer sheath of a lead body. See, for example, U.S. Pat. Nos. 4,521,564, 5,308,641, 5,811,151, 5,866,113, 5,925,552, 6,033,719, 6,096,070, 6,159,531, 6,961,610, 7,632,234, and U.S. Patent Applications 2003/0059537, 2006/0240072, and 2008/0063627. Also included are methods of modifying the outer surface of an implantable medical electrical lead by covalently attaching one or more biological agents that promote endothelialization to the polymeric material of the outer insulative sheath of the lead body.

In other embodiments, the one or more biological agents that promote endothelialization may be applied to the insulative outer sheath of the lead body in a manner other than covalent attachment. For example, one or more biological agents that promote endothelialization may be applied to the insulative outer sheath of the lead body by coating, immersion, dipping, spraying, vapor deposition, plasma deposition, and the like.

The method of covalently attaching a biological agent that promotes endothelialization will differ depending on the nature of the biological agent and/or the material of polymeric coating of the outer sheath of the lead. When the agent is an antibody or protein, covalently bonding the protein to the surface with outer sheath with bi-functional molecules such as glutaraldehyde, carbodiimides, biotin-avidin, and other molecules with one or more functional groups on each of at least two ends as are well known to those skilled in the art. Additionally, bi-functional spacer molecules such as N-hydroxysuccinimide derivatized polyethylene glycols may be used to bind the protein.

Figure 3:
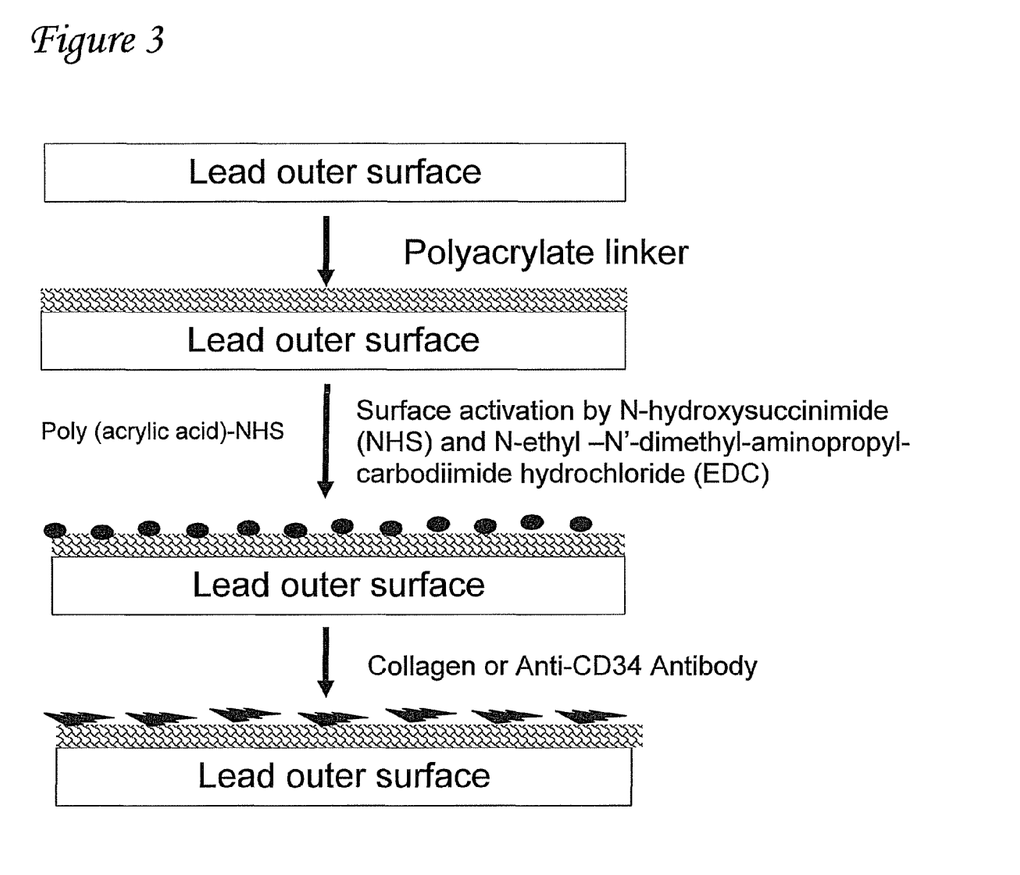
FIG. 3 presents an overview covalent attachment to lead outer surface by activation of reactive compounds N-hydroxysuccinimide (NHS) and N-ethyl-N'-dimethyl-aminopropyl-carbodiimide hydrochloride (EDC).
Figure 4:
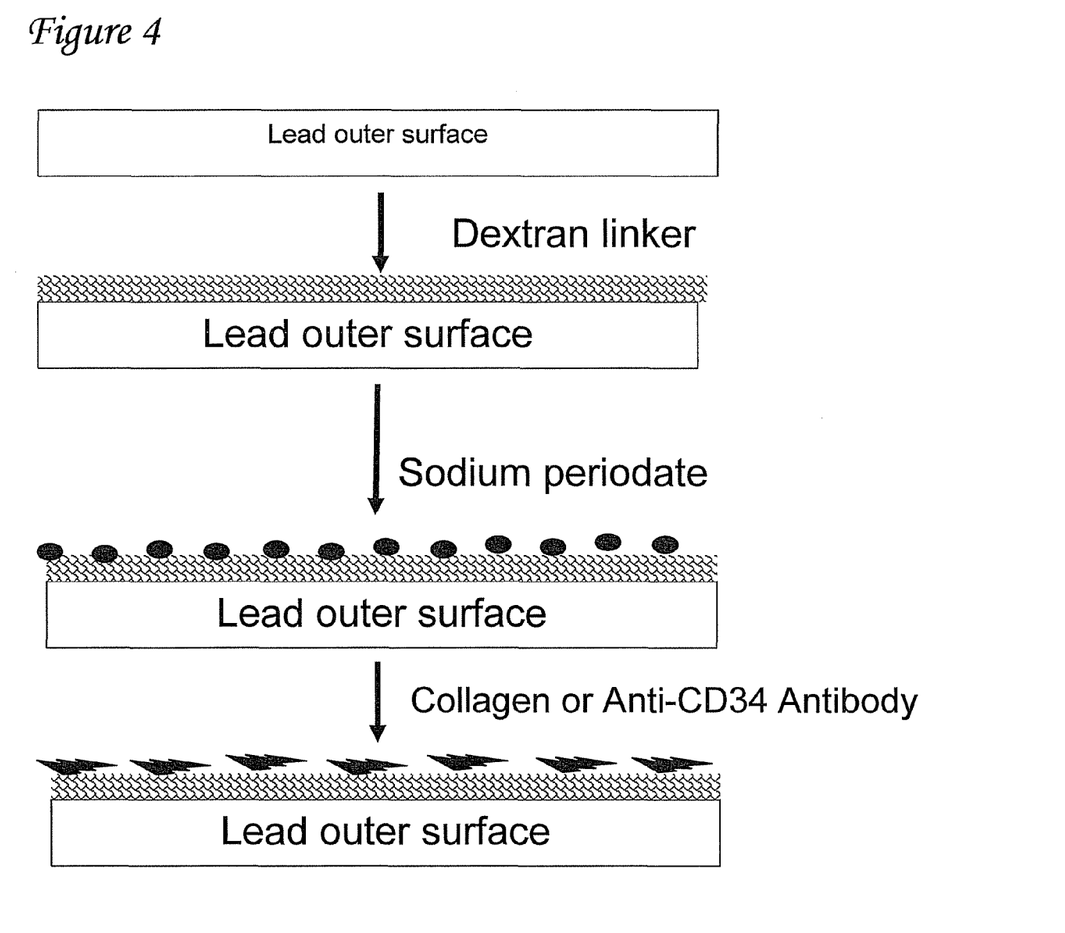
FIG. 4 presents an overview covalent attachment to lead outer surface with use of a dextran linker and sodium periodate chemistry.

Covalent attachment may be accomplished by one or more reactive compounds, such as, for example, activation by N-hydroxysuccinimide (NHS) and N-ethyl-N'-dimethyl-aminopropyl-carbodiimide hydrochloride (EDC), as described in FIG. 3. Additional reactive groups may include (3-aminopropyl)trimethoxysilane (APTS), epichlorohydrin (EPC), star PEG-succinimidyl succinate, dextran (DEX), and/or polyacrylic acid (see, for example, U.S. Published Patent Application Serial No. 2009/0270962). The outer sheath of the lead may be, for example, a polymeric material having surface modifying end groups that facilitate the attachment of a biological agent. For example, a branched polyethylene oxide (PEO) or star PEO, as described, for example, in U.S. Pat. No. 6,961,610, may serve as the polymer outer sheath of a lead. These compounds are commercially available, for example, from Sigma-Aldrich located in St. Louis, Mo. Covalent attachment may also be accomplished by the use of a dextran linker and sodium periodate chemistry, as described in FIG. 4.

Figure 5:
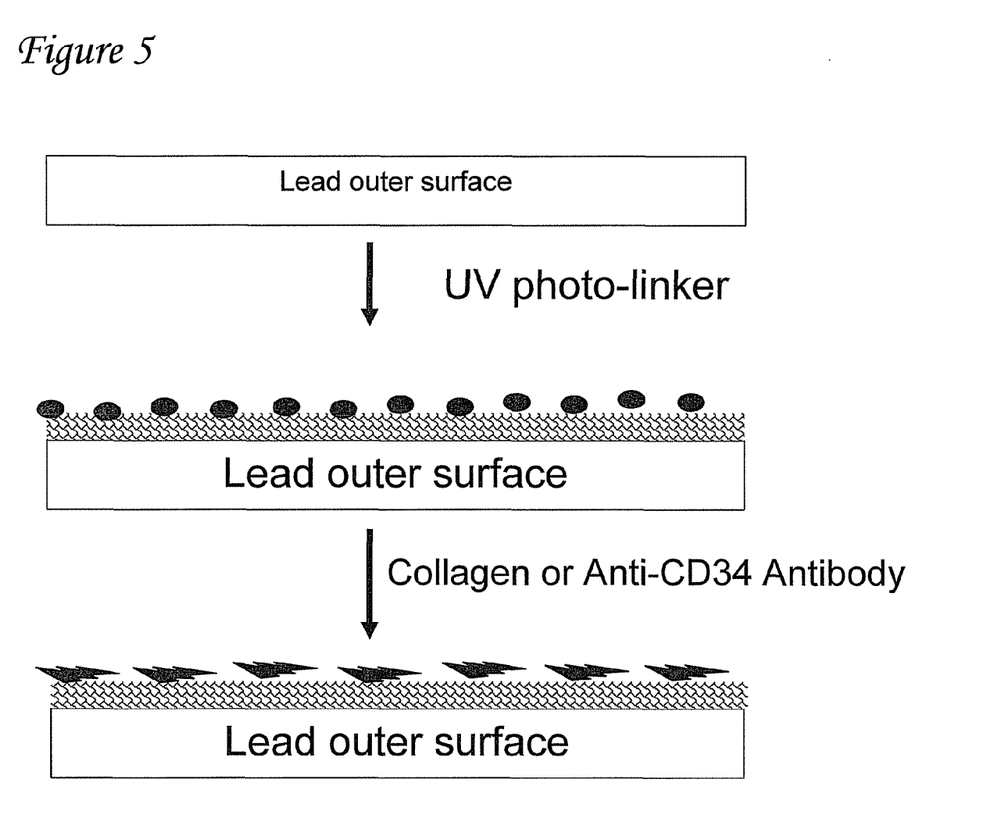
FIG. 5 presents an overview covalent attachment to lead outer surface with UV photo-linker technology.

Covalent attachment may be accomplished by photo-coupling techniques, via one or more activated photoreactive groups that are activated and reacted to bond one or more biological agents to the outer sheath of the lead. "Activated" means that the photoreactive groups have been treated with an activating source of radiation, thereby having excited the groups to an active state that resulted in bonding the groups to the tissue graft material. Photoreactive groups, broadly defined, are groups that respond to specific applied external light energy to undergo active specie generation with resultant covalent bonding to a target. Photoreactive groups are those groups of atoms in a molecule that retain their covalent bonds unchanged under conditions of storage but which, upon activation, form covalent bonds with other molecules. The photoreactive groups generate active species such as free radicals, nitrenes, carbenes, and excited states of ketones upon absorption of external electromagnetic or kinetic (thermal) energy. Photoreactive groups may be chosen to be responsive to various portions of the electromagnetic spectrum. For example, those that are responsive to the ultraviolet and visible portions of the spectrum may be used. Such photoreactive groups are well known in the art (see, for example, U.S. Patent Application Serial No. 2008/0063627). Photoreactive groups, including, but not limited to the UV photo-linker technology described in FIG. 5.

As used herein, a biological agent is a biomolecule that engages in a biological activity. A biological agent that promotes endothelialization may be, for example, a polypeptide, a peptide, a polysaccharide, an antibody, or an aptamer. As used herein, a polypeptide (also referred to herein as a "protein") is a chain of fifty or more amino acids. As used herein, a peptide is a chain of at least two, but fewer than fifty amino acids.

A biological agent that promotes endothelialization may be, for example, a peptide. Such peptides include, but are not limited to, peptides containing the Arg-Gly-Asp (RGD) fibronectin-derived attachment peptide and peptides containing the laminin-derived adhesive peptides Cys-Asp-Pro-Gly-Tyr-Ile-Gly-Ser-Arg ((CDPGYIGSR); (SEQ ID NO:1)), Tyr-Ile-Gly-Ser-Arg ((YIGSR); (SEQ ID NO:2)), or Tyr-Ile-Gly-Ser-Arg-Gly ((YIGSRG); (SEQ ID NO:3)).

A biological agent that promotes endothelialization may be, for example, a polypeptide. Such polypeptides include, but are not limited to, extracellular matrix (ECM) proteins, such as, for example, collagen, laminin, fibronectin, vitronectin, or matrigel; growth factors, such as for example, basic fibroblast growth factor (bFGF), transforming growth factor-$\beta$ (TGF-$\beta$), vascular endothelial growth factor (VEGF), or granulocyte colony stimulating factor (G-CSF); cytokines; or hormones. In some preferred embodiments, the polypeptide is collagen, including, but not limited to, collagen I and/or collagen IV. Also included are polypeptides containing the RGD, CDPGYIGSR (SEQ ID NO:1), YIGSR (SEQ ID NO:2), or YIGSRG (SEQ ID NO:3) attachment recognition sequences.

A biological agent that promotes endothelialization may be, for example, a polysaccharide, such as for example, amylose, maltodextrin, amylopectin, starch, dextran, hyaluronic acid, heparin, chondroitin sulfate, dermatan sulfate, heparan sulfate, keratan sulfate, dextran sulfate, pentosan polysulfate, or chitosan. In some preferred embodiments, the polysaccharide is hyaluronic acid (HA; also known as hyalurnan or hyaluronate), including, for example, a mixture of large HA fragments (with a molecular weight of greater than about 10 kiloDalton (kDa) and less than about 1 megadalton (Mda)), high molecular weight (HMW) HA (with a molecular weight of greater than about 1000 kDa), an oligomeric HA mixture (HA-o) (with, for example, a molecular weight of about 0.75 to about 10 kDa), HA-1500 (with a molecular weight of about 1500 kDa), HA 1500-3000 (with a molecular weight range of about 1500 daltons to about 3000 daltons), HA-1500 (with a molecular weight of about 1500 Da), and purified oligomers of HA, such as HA-6-mer or HA 12-mer.

A biological agent that promotes endothelialization may be, for example, an apatamer. Aptamers are single stranded DNA or RNA polynucleotides (ssDNA or ssRNA), generally about 70 to 80 nucleotides in length, that can bind with a high affinity and specificity to a target molecule, such as for example, a target molecule on the surface of an endothelial cell or an endothelial progenitor cell, including, but not limited to, VE-cadherin; CD146 (also known as MCAM or MUC18); CD31 (also known as PECAM-1); CD117 (also know as stem cell receptor factor (SCF R)); CD34 (also known as hemopoietic progenitor cell antigen 1 (HPCA1) and gp105-120); Tie-2; CD45; vascular endothelial growth factor receptor 1 (VEGF R1); vascular endothelial growth factor receptor 2 (VEGF R2; also know as KDR and Flk-1); CXCR4; VEGF R3 (also known as Flt-4); CD133; and E-selectin. Aptamers are generated through an iterative in vitro selection and amplification process called SELEX (systematic evolution of ligands by exponential enrichment).

A biological agent that promotes endothelialization may be, for example, an antibody. Such an antibody may be, for example, an antibody that binds to a surface molecule on circulating endothelial progenitor cells. Endothelial progenitor cells (EPCs) are a type of predifferentiated adult stem cell with the potential to proliferate and differentiate into mature endothelial cells. EPCs are mainly located in the bone marrow, but circulate at low concentrations in the peripheral blood of healthy adults. The concentration of EPCs in peripheral blood can be increased by mobilization with growth factors such as, for example, granulocyte stimulating factor (G-CSF) or VEGF. EPCs have the potential to proliferate and differentiate mature endothelial cells, prompting the process of endothelialization, with the capacity to repair or form new endothelium. See, for example, Avci-Adali et al., 2008, *Biomaterials;* 29:3936-3945; Chong et al., 2010, *Tissue Eng Part A;* 16(8):2485-2495; Li et al., 2010, *J Biomed Mater Res A;* 94(4):1283-93; Lin et al., 2010, *Biomaterials;* 31: 4017-4025; and Wendel et al., 2010, *Int J Cardiol;* 145(1):115-7.

Markers for endothelial progenitor cells include, but are not limited to, VE-cadherin; CD146 (also known as MCAM or MUC18); CD31 (also known as PECAM-1); CD117 (also know as stem cell receptor factor (SCF R)); CD34 (also known as hemopoietic progenitor cell antigen 1 (HPCA1) and gp105-120); Tie-2; CD45; VEGF R2 (also know as KDR and Flk-1); CXCR4; and VEGF R3 (also known as Flt-4). In some embodiments, the antibody may be a human antibody or a humanized antibody.

In some preferred embodiments, the antibody is an antibody to CD34, including, but not limited to, an antibody to human CD34. CD34 is a monomeric cell surface antigen with a molecular mass of approximately 110 kD that is selectively expressed on human hematopoietic progenitor cells. Although its precise biological function remains unknown, the pattern of expression of CD34 suggest that it plays a significant role in early hematopoieses and it is used a surface marker for very early hematopoietic stem cells. Cells expressing CD34 (CD34+ cell) are normally found in the umbilical cord and bone marrow as hematopoietic cells, a subset of mesenchymal stem cells, endothelial progenitor cells, and endothelial cells of blood vessels. Antibodies to CD34 include monoclonal antibodies 4C8, BI-3C5 (Santa Cruz Biotechnology, Inc.); IC-H3; MY10; 188.27; Clone 4H11 (BioLegend, San Diego, Calif.); Clone 561 (BioLegend, San Diego, Calif.); Clone 581 (BioLegend, San Diego, Calif.); and rabbit monoclonal CD34 antibodies clone ID EP373Y (Epitomics, Inc., Burlingame, Calif.) and Clone ID EPR2999 (Epitomics, Inc., Burlingame, Calif.).

A biological agent that promotes endothelialization may be, for example, a ligand to a receptor or other surface protein on the surface of circulating endothelial progenitor cells, such as, for example, a ligand to VE-cadherin; CD146 (also known as MCAM or MUC18); CD31 (also known as PECAM-1); CD117 (also know as stem cell receptor factor (SCF R)); CD34 (also known as hemopoietic progenitor cell antigen 1 (HPCA1) and gp105-120); Tie-2; CD45; VEGF R2 (also know as KDR and Flk-1); CXCR4; and VEGF R3 (also known as Flt-4). In some preferred embodiments, the biological agent that promotes endothelialization is a ligand to CD34.

In some embodiments, a medical electrical lead is coated with one biological agent that promotes endothelialization. In some embodiments, a medical electrical lead is coated with two or more biological agents that promote endothelialization, including, but not limited to any two, three, four, five, or more of the biological agent that promote endothelialization described herein. A medical electrical lead may be further coated with additional compounds.

It is understood that the present invention is not limited for use in cardiac leads. Other uses of the coated leads described herein include use in other locations where thrombus formation is problematic and/or where the endothelialization of the leads would be clinically advantageous. Medical electrical leads, as described herein, may for example, be used for neurostimulation. In some embodiments, medical electrical leads may be chronically implanted in a subject.

Medical electrical leads, as described herein, may be used any appropriate diagnostic or therapeutic procedure, including, but not limited to, use in conjunction with systems, devices, methods, and apparatus in which the transmission and/or reception of one or more electrical impulses in a subject is desired. For example, medical electrical leads, as described herein, may be used in any of a variety of therapeutic methods. Medical electrical leads as described herein may be used along with a device that is implantable (in whole or in part), also referred to as an implantable medical device (IMD). An IMD may be, for example, an implantable pulse generator (IPG) that delivers electronic pacing therapy. Any of a wide variety of implantable electronic pulse generators may be used, including, but not limited to, pacemaker, implantable cardioverter defibrillator (ICD), cardiac resynchronization therapy (CRT), cardiac resynchronization therapy defibrillation device (CRT-D), subcutaneous ICD (SubQ ICD), intravascular pacemaker/ICD, and/or miniaturized leadless pacemaker. A pacemaker may include, but is not limited to, EnRhythm® pacemaker, Adapta® pacemaker, Versa™ pacemaker, Sensia™ pacemaker, Thera® pacemaker, Prodigy® pacemaker, Priva® pacemaker, and Minuet® pacemaker, all available from Medtronic Inc., Minneapolis, Minn. An IMD may, for example, provide cardiac monitoring capabilities, alternate cardiac therapies, non-cardiac monitoring and/or non-cardiac therapies.

As used herein, the term "subject" includes, but is not limited to, humans and non-human vertebrates. In preferred embodiments, a subject is a mammal, particularly a human. A subject may be an individual. A subject may be a patient. Non-human vertebrates include livestock animals, companion animals, and laboratory animals. Non-human subjects also include non-human primates as well as rodents, such as, but not limited to, a rat or a mouse. Non-human subjects also include, without limitation, chickens, horses, cows, pigs, goats, dogs, cats, guinea pigs, hamsters, mink, and rabbits.

The methods of the present invention include in vitro, ex vivo, and in vivo methods. As used herein "in vitro" is in cell culture and "in vivo" is within the body of a subject.

A coated medical electrical lead as described herein may be placed within the heart of a subject. That is, a heart having an epicardial surface and disposed within a torso.

The endothelialization of a coated medical electrical lead may be monitored in vivo, for example, as described in the examples included herewith, or in vitro, for example, by testing for the adhesion of isolated human endothelial cells, or progenitors thereof, to a lead.

As used herein, "isolated" refers to material that has been either removed from its natural environment (e.g., the natural environment if it is naturally occurring), produced using recombinant techniques, or chemically or enzymatically synthesized, and thus is altered "by the hand of man" from its natural state.

The present invention is illustrated by the following examples. It is to be understood that the particular examples, materials, amounts, and procedures are to be interpreted broadly in accordance with the scope and spirit of the invention as set forth herein.

EXAMPLES

Example 1

Endothelialization of Collagen Coated Leads

Material and Methods

Test Animals. Six adult purpose-bred rabbits of either sex, weighing >3.0 kg at the time of surgery, were used in this study.

Study Design. The study consisted of two groups of three rabbits each. One group of three rabbits received a single uncoated aorta tubing (control group), while a second group of three rabbits received a coated aortic tubing with a photografted collagen monolayer. The aortic tubings were implanted via a left carotid artery stick. All rabbits were euthanized on postoperative day 28. At the time of necropsy and tissue analysis, the pathology was blinded towards the groupings.

Implant Materials. The aortic tubings were 4 French, 6 inch long polyurethane Elasthane 55D tubings (without wax), with an MP35N inner coil, and sealed at both ends with silicone medical adhesive. Coated aortic tubings received a photografted Collagen I monolayer coating. Control aortic tubings were uncoated. Aortic tubings were not electrically active.

Necropsy Methods and Tissue Trimming. The skin over the thorax and the neck was removed, the leads along the neck were located, and the right side of the rib cage was opened. After reflection of the lungs, the pericardium was incised and the epicardial surface of the heart inspected. The aorta was also visualized. The left side of the heart was also opened and examined. After the aorta was opened longitudinally, the tubing was located, and imaged in situ. Heart, aorta, and aortic tubing were immersed in 10% neutral-buffered formalin. The major organs without the brain were examined.

Histological review of tubing was performed. First, the metal coil was extracted. Then the distal tips were cut off and were transferred into Karnovsky solution for post fixation. These tips were forwarded for confocal microscopy and scanning electron microscopy (SEM). A histological review was also preformed on the adjacent portion of the aortic tubing that was free floating in the LV or aorta (and not surrounded by carotid artery); it was cut longitudinally in two halves and forwarded for histology. Remainder of fixed tissue samples were returned to formalin for continued preservation.

Slide Preparation/Histology Methods. Specimens within labeled histology cassettes were dehydrated through a graded series of alcohol and embedded in paraffin. Three to 5 μm thick paraffin sections were cut with a microtome, mounted on glass slides, deparaffinized, and stained with hematoxylin and eosin (HE) to evaluate morphology. A serial section of the tissue sections was stained with Trichrome Masson to evaluate connective tissue. Microscopic measurements were performed by using the Nikon Digital Sight Camera (Model DS-5M). Brightfield histology images were captured with a Nikon Digital Sight Camera that was attached to a Nikon Ecclipse 80I brightfield microscope.

Results

Gross images and histology images were obtained for the aortic tubings after formalin fixation. All the three coated tubings demonstrated endothelial cell overgrowth, while only one of the three uncoated control tubings demonstrated limited endothelial cell overgrowth. Two of the three uncoated tubings showed no endothelial cell overgrowth. Confocal microscopy results and SEM yielded similar results as brightfield histology. Thus, a photografted collagen monolayer on polyurethane 55D leads, implanted in aorta in six rabbits for twenty-eight days, promoted endotheliazation as compared to uncoated polyurethane 55D leads.

Following procedures described above, the endothelialization of leads coated with anti-CD34 antibodies will also be determined.

The complete disclosure of all patents, patent applications, and publications, and electronically available material (including, for instance, nucleotide sequence submissions in, e.g., GenBank and RefSeq, and amino acid sequence submissions in, e.g., SwissProt, PR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims. All headings are for the convenience of the reader and should not be used to limit the meaning of the text that follows the heading, unless so specified.

What is claimed is:

1. An implantable electrical lead comprising an external blood contacting surface comprising an external coating comprising a monolayer of at least one biological agent that promotes endothelialization covalently attached to a polymeric lead surface, the biological agent comprising a polypeptide, the polypeptide comprising collagen.

2. A method comprising implanting a lead of claim 1 in a left chamber of the heart.

3. The method of claim 2 further comprising delivering an electrical stimulus to the heart through the lead.

4. The method of claim 2 further comprising sensing an electrical signal through the lead.

5. The implantable electrical lead of claim 1, wherein the lead is a stimulation lead.

6. The implantable electrical lead of claim 1, wherein the lead is a sensing lead.

7. The implantable electrical lead of claim 1, wherein the lead is suitable for placement in the left ventricle of the heart.

8. A method for left lead placement, the method comprising placing a lead of claim 1 in the left ventricle of the heart.

9. A method for endothelializing an electrical lead placed in the left ventricle of the heart, the method comprising placing a lead of claim 1 in the left ventricle of the heart.

10. A method for promoting the endothelialization of an electrical lead placed in the left ventricle of the heart, the method comprising placing a lead of claim 1 in the left ventricle of the heart.

11. An implantable electrical lead comprising an external blood contacting surface comprising an external coating comprising a monolayer of at least one biological agent that promotes endothelialization covalently attached to a polymeric lead surface, the biological agent comprising an antibody.

12. The implantable electrical lead of claim 11, the antibody comprising an antibody to an endothelial cell surface marker.

13. The implantable electrical lead of claim 12, the antibody comprising an anti-CD34 antibody.

14. The implantable electrical lead of claim 11, wherein the lead is a stimulation lead.

15. The implantable electrical lead of claim 11, wherein the lead is a sensing lead.

16. The implantable electrical lead of claim 11, wherein the lead is suitable for placement in the left ventricle of the heart.

17. An implantable electrical lead comprising an external blood contacting surface comprising an external coating comprising a monolayer of at least one biological agent that promotes endothelialization covalently attached to a polymeric lead surface, the biological agent comprising a polysaccharide.

18. The implantable electrical lead of claim 17, wherein the lead is a stimulation lead.

19. The implantable electrical lead of claim 17, wherein the lead is a sensing lead.

20. The implantable electrical lead of claim 17, wherein the lead is suitable for placement in the left ventricle of the heart.

* * * * *

SEQUENCE LISTING

```
<160> NUMBER OF SEQ ID NOS: 3

<210> SEQ ID NO 1
<211> LENGTH: 9
<212> TYPE: PRT
<213> ORGANISM: artificial
<220> FEATURE:
<223> OTHER INFORMATION: peptide containing a laminin-derived adhesive
```

```
                    peptide

<400> SEQUENCE: 1

Cys Asp Pro Gly Tyr Ile Gly Ser Arg
1               5

<210> SEQ ID NO 2
<211> LENGTH: 5
<212> TYPE: PRT
<213> ORGANISM: artificial
<220> FEATURE:
<223> OTHER INFORMATION: peptide containing a laminin-derived adhesive
      peptide

<400> SEQUENCE: 2

Tyr Ile Gly Ser Arg
1               5

<210> SEQ ID NO 3
<211> LENGTH: 6
<212> TYPE: PRT
<213> ORGANISM: artificial
<220> FEATURE:
<223> OTHER INFORMATION: peptide containing a laminin-derived adhesive
      peptide

<400> SEQUENCE: 3

Tyr Ile Gly Ser Arg Gly
1               5
```